(12) United States Patent
Dasnurkar et al.

(10) Patent No.: US 11,564,692 B2
(45) Date of Patent: Jan. 31, 2023

(54) OCCLUSION SYSTEMS

(71) Applicant: Terumo Corporation, Tokyo (JP)

(72) Inventors: Anup Dasnurkar, Rancho Santa Margarita, CA (US); Brian Gray, Aliso Viejo, CA (US); Maricela Walker, Lake Forest, CA (US); Frida San, Long Beach, CA (US); Michael Martel, Orange, CA (US)

(73) Assignee: Terumo Corporation, Tokyo (JP)

( * ) Notice: Subject to any disclaimer, the term of this patent is extended or adjusted under 35 U.S.C. 154(b) by 582 days.

(21) Appl. No.: 16/672,273

(22) Filed: Nov. 1, 2019

(65) Prior Publication Data

US 2020/0138448 A1 May 7, 2020

Related U.S. Application Data

(60) Provisional application No. 62/754,493, filed on Nov. 1, 2018.

(51) Int. Cl.
*A61B 17/12* (2006.01)
*A61B 17/00* (2006.01)

(52) U.S. Cl.
CPC .. *A61B 17/12136* (2013.01); *A61B 17/12109* (2013.01); *A61B 2017/0065* (2013.01)

(58) Field of Classification Search
CPC ........ A61B 17/12136; A61B 17/00491; A61B 17/12122; A61B 17/12186; A61B 17/12022; A61B 2017/005; A61B 2017/0065; A61B 17/0057; A61B 17/12031; A61B 17/12113; A61B 2017/00876; A61B 2017/1205; A61B 2017/12054; A61B 17/12109; A61B 17/12168; A61B 17/12195; A61B 2017/00557; A61B 2017/00575; A61M 2025/1054; A61M 25/10; A61M 2025/1013; A61M 2025/105; A61M 2025/1052

See application file for complete search history.

(56) References Cited

U.S. PATENT DOCUMENTS

| | | |
|---|---|---|
| 3,448,739 A | 6/1969 | Stark et al. |
| 4,364,392 A | 12/1982 | Strother et al. |
| 5,041,090 A | 8/1991 | Scheglov et al. |
| 5,067,489 A | 11/1991 | Lind |

(Continued)

FOREIGN PATENT DOCUMENTS

| | | | | |
|---|---|---|---|---|
| CN | 102438533 A | | 5/2012 | |
| EP | 0352325 | * | 1/1990 | ............. A61B 17/12 |

(Continued)

OTHER PUBLICATIONS

WIPO, U.S. International Search Authority, International Search Report and Written Opinion dated Jan. 3, 2020 in International Patent Application No. PCT/US2019/059543, 9 pages.

(Continued)

*Primary Examiner* — Katherine M Shi
(74) *Attorney, Agent, or Firm* — Inskeep IP Group, Inc.

(57) ABSTRACT

An occlusion device with particular utility in occlusion of left atrial appendages is described. The occlusion device embodiments utilize an inflatable balloon or expandable element used to occlude the treatment site.

19 Claims, 13 Drawing Sheets

(56) References Cited

U.S. PATENT DOCUMENTS

| | | |
|---|---|---|
| 5,122,136 A | 6/1992 | Guglielmi et al. |
| 5,330,483 A | 7/1994 | Heaven et al. |
| 5,334,210 A | 8/1994 | Gianturco |
| 5,354,309 A | 10/1994 | Schnepp-Pesch et al. |
| 5,397,331 A | 3/1995 | Himpens et al. |
| 5,466,242 A | 11/1995 | Mori |
| 5,496,277 A | 3/1996 | Termin et al. |
| 5,499,995 A | 5/1996 | Teirstein |
| 5,514,093 A | 5/1996 | Ellis et al. |
| 5,662,711 A | 9/1997 | Douglas |
| 5,713,848 A | 2/1998 | Dubrul |
| 5,718,159 A | 2/1998 | Thompson |
| 5,725,552 A | 3/1998 | Kotula et al. |
| 5,741,333 A | 4/1998 | Frid |
| 5,814,062 A | 9/1998 | Sepetka et al. |
| 5,814,064 A | 9/1998 | Daniel et al. |
| 5,846,261 A | 12/1998 | Kotula et al. |
| 5,853,422 A | 12/1998 | Huebsch et al. |
| 5,861,003 A | 1/1999 | Latson et al. |
| 5,919,224 A | 7/1999 | Thompson et al. |
| 5,925,060 A | 7/1999 | Forber |
| 5,941,896 A | 8/1999 | Kerr |
| 5,944,738 A | 8/1999 | Amplatz et al. |
| 5,947,997 A | 9/1999 | Pavcnik et al. |
| 5,954,745 A | 9/1999 | Gertler et al. |
| 6,010,498 A | 1/2000 | Guglielmi |
| 6,019,786 A | 2/2000 | Thompson |
| 6,022,336 A | 2/2000 | Zadno-Azizi et al. |
| 6,024,754 A | 2/2000 | Engelson |
| 6,027,520 A | 2/2000 | Tsugita et al. |
| 6,059,814 A | 5/2000 | Ladd |
| 6,066,149 A | 5/2000 | Samson et al. |
| 6,113,641 A | 9/2000 | Leroy et al. |
| 6,142,987 A | 11/2000 | Tsugita |
| 6,152,144 A | 11/2000 | Lesh et al. |
| 6,176,873 B1 | 1/2001 | Ouchi |
| 6,346,117 B1 | 2/2002 | Greenhalgh |
| 6,375,668 B1 | 4/2002 | Gifford et al. |
| 6,379,329 B1 | 4/2002 | Naglreiter et al. |
| 6,428,557 B1 | 8/2002 | Hilaire |
| 6,428,558 B1 | 8/2002 | Jones et al. |
| 6,451,048 B1 | 9/2002 | Berg et al. |
| 6,468,303 B1 | 10/2002 | Amplatz et al. |
| 6,550,177 B1 | 4/2003 | Epple, Jr. |
| 6,585,748 B1 | 7/2003 | Jeffree |
| 6,589,265 B1 | 7/2003 | Palmer et al. |
| 6,652,555 B1 | 11/2003 | VanTassel et al. |
| 6,685,748 B1 | 2/2004 | Day et al. |
| 6,802,851 B2 | 10/2004 | Jones et al. |
| 6,811,560 B2 | 11/2004 | Jones et al. |
| 6,953,472 B2 | 10/2005 | Palmer et al. |
| 6,994,717 B2 | 2/2006 | Kónya et al. |
| 7,083,632 B2 | 8/2006 | Avellanet et al. |
| 7,122,058 B2 | 10/2006 | Levine et al. |
| 7,195,636 B2 | 3/2007 | Avellanet et al. |
| 7,229,461 B2 | 6/2007 | Chin et al. |
| 7,267,694 B2 | 9/2007 | Levine et al. |
| 7,294,146 B2 | 11/2007 | Chew et al. |
| 7,306,624 B2 | 12/2007 | Yodfat et al. |
| 7,320,065 B2 | 1/2008 | Gosior et al. |
| 7,329,285 B2 | 2/2008 | Levine et al. |
| 7,569,066 B2 | 8/2009 | Gerberding et al. |
| 7,632,391 B2 | 12/2009 | Cochran |
| 7,645,259 B2 | 1/2010 | Goldman |
| 7,665,466 B2 | 2/2010 | Figulla et al. |
| 7,678,129 B1 | 3/2010 | Gesswein et al. |
| 7,691,124 B2 | 4/2010 | Balgobin |
| 7,695,488 B2 | 4/2010 | Berenstein et al. |
| 7,713,282 B2 | 5/2010 | Frazier et al. |
| 7,749,238 B2 | 7/2010 | Corcoran et al. |
| 7,762,943 B2 | 7/2010 | Khairkhahan |
| 7,981,151 B2 | 7/2011 | Rowe |
| 8,034,061 B2 | 10/2011 | Amplatz et al. |
| 8,043,326 B2 | 10/2011 | Hancock et al. |
| 8,060,183 B2 | 11/2011 | Leopold et al. |
| 8,062,251 B2 | 11/2011 | Goldman |
| 8,066,732 B2 | 11/2011 | Paul et al. |
| 8,083,792 B2 | 12/2011 | Boucher et al. |
| 8,142,456 B2 | 3/2012 | Rosqueta et al. |
| 8,152,833 B2 | 4/2012 | Zaver et al. |
| 8,251,948 B2 | 8/2012 | Goldman |
| 8,262,719 B2 | 9/2012 | Erickson et al. |
| 8,280,486 B2 | 10/2012 | Miller et al. |
| 8,308,752 B2 | 11/2012 | Tekulve |
| 8,313,505 B2 | 11/2012 | Amplatz et al. |
| 8,352,014 B2 | 1/2013 | Leipold et al. |
| 8,357,180 B2 | 1/2013 | Feller, III et al. |
| 8,361,111 B2 | 1/2013 | Widomski et al. |
| 8,361,138 B2 | 1/2013 | Adams |
| 8,398,670 B2 | 3/2013 | Amplatz et al. |
| 8,408,212 B2 | 4/2013 | O'Brien et al. |
| 8,425,548 B2 | 4/2013 | Connor |
| 8,433,391 B2 | 4/2013 | Mark |
| 8,442,623 B2 | 5/2013 | Nicoson et al. |
| 8,454,633 B2 | 6/2013 | Amplatz et al. |
| 8,460,366 B2 | 6/2013 | Rowe |
| 8,480,702 B2 | 7/2013 | Kusleika et al. |
| 8,491,612 B2 | 7/2013 | Stopek et al. |
| 8,523,940 B2 | 9/2013 | Richardson et al. |
| 8,636,760 B2 | 1/2014 | Garcia et al. |
| 8,663,301 B2 | 3/2014 | Riina et al. |
| 8,671,815 B2 | 3/2014 | Hancock et al. |
| 8,679,150 B1 | 3/2014 | Janardhan et al. |
| 8,685,055 B2 | 4/2014 | VanTassel et al. |
| 8,690,907 B1 | 4/2014 | Janardhan et al. |
| 8,696,701 B2 | 4/2014 | Becking et al. |
| 8,715,314 B1 | 5/2014 | Janardhan et al. |
| 8,715,315 B1 | 5/2014 | Janardhan et al. |
| 8,715,316 B1 | 5/2014 | Janardhan et al. |
| 8,715,317 B1 | 5/2014 | Janardhan et al. |
| 8,715,338 B2 | 5/2014 | Frid |
| 8,721,676 B1 | 5/2014 | Janardhan et al. |
| 8,721,677 B1 | 5/2014 | Janardhan et al. |
| 8,721,707 B2 | 5/2014 | Boucher et al. |
| 8,728,112 B2 | 5/2014 | Evert et al. |
| 8,728,116 B1 | 5/2014 | Janardhan et al. |
| 8,728,117 B1 | 5/2014 | Janardhan et al. |
| 8,728,141 B2 | 5/2014 | Riina et al. |
| 8,733,618 B1 | 5/2014 | Janardhan et al. |
| 8,734,483 B2 | 5/2014 | Tekulve et al. |
| 8,735,777 B1 | 5/2014 | Janardhan et al. |
| 8,747,432 B1 | 6/2014 | Janardhan et al. |
| 8,747,453 B2 | 6/2014 | Amplatz et al. |
| 8,747,462 B2 | 6/2014 | Hill et al. |
| 8,747,597 B2 | 6/2014 | Rosqueta et al. |
| 8,753,371 B1 | 6/2014 | Janardhan et al. |
| 8,758,426 B2 | 6/2014 | Hood et al. |
| 8,764,772 B2 | 7/2014 | Tekulve |
| 8,764,787 B2 | 7/2014 | Ren |
| 8,777,974 B2 | 7/2014 | Amplatz et al. |
| 8,777,979 B2 | 7/2014 | Shrivastava et al. |
| 8,778,008 B2 | 7/2014 | Amplatz et al. |
| 8,783,151 B1 | 7/2014 | Janardhan et al. |
| 8,784,446 B1 | 7/2014 | Janardhan et al. |
| 8,789,452 B1 | 7/2014 | Janardhan et al. |
| 8,790,365 B1 | 7/2014 | Janardhan et al. |
| 8,795,316 B2 | 8/2014 | Balgobin et al. |
| 8,795,319 B2 | 8/2014 | Ryan et al. |
| 8,795,330 B1 | 8/2014 | Janardhan et al. |
| 8,803,030 B1 | 8/2014 | Janardhan et al. |
| 8,813,625 B1 | 8/2014 | Janardhan et al. |
| 8,816,247 B1 | 8/2014 | Janardhan et al. |
| 8,821,529 B2 | 9/2014 | Kariniemi et al. |
| 8,821,849 B2 | 9/2014 | Schwartz |
| 8,828,043 B2 | 9/2014 | Chambers |
| 8,828,045 B1 | 9/2014 | Janardhan et al. |
| 8,828,051 B2 | 9/2014 | Javois et al. |
| 8,845,678 B1 | 9/2014 | Janardhan et al. |
| 8,845,679 B1 | 9/2014 | Janardhan et al. |
| 8,852,227 B1 | 10/2014 | Janardhan et al. |
| 8,859,934 B1 | 10/2014 | Janardhan et al. |
| 8,863,631 B1 | 10/2014 | Janardhan et al. |
| 8,866,049 B1 | 10/2014 | Janardhan et al. |
| 8,869,670 B1 | 10/2014 | Janardhan et al. |

(56) References Cited

U.S. PATENT DOCUMENTS

| | | |
|---|---|---|
| 8,870,901 B1 | 10/2014 | Janardhan et al. |
| 8,870,910 B1 | 10/2014 | Janardhan et al. |
| 8,872,068 B1 | 10/2014 | Janardhan et al. |
| 8,876,849 B2 | 11/2014 | Kratzberg et al. |
| 8,882,787 B2 | 11/2014 | Brenzel et al. |
| 8,882,797 B2 | 11/2014 | Janardhan et al. |
| 8,895,891 B2 | 11/2014 | Janardhan et al. |
| 8,900,287 B2 | 12/2014 | Amplatz et al. |
| 8,904,914 B2 | 12/2014 | Janardhan et al. |
| 8,905,961 B2 | 12/2014 | Braido et al. |
| 8,906,057 B2 | 12/2014 | Connor et al. |
| 8,910,555 B2 | 12/2014 | Janardhan et al. |
| 8,945,170 B2 | 2/2015 | Paul, Jr. |
| 9,011,476 B2 | 4/2015 | Sideris |
| 9,295,571 B2 | 3/2016 | Newell et al. |
| 9,579,104 B2 | 2/2017 | Beckham et al. |
| 9,770,234 B2 | 9/2017 | Sideris et al. |
| 10,405,866 B2 | 9/2019 | Chakraborty et al. |
| 2001/0000797 A1 | 5/2001 | Mazzochi |
| 2001/0012949 A1 | 8/2001 | Forber |
| 2002/0042628 A1 | 4/2002 | Chin et al. |
| 2002/0082638 A1 | 6/2002 | Porter et al. |
| 2002/0111647 A1 | 8/2002 | Khairkhahan et al. |
| 2002/0123759 A1 | 9/2002 | Amplatz |
| 2002/0143349 A1 | 10/2002 | Gifford, III et al. |
| 2002/0156499 A1 | 10/2002 | Konya et al. |
| 2002/0165572 A1 | 11/2002 | Saadat |
| 2002/0189727 A1 | 12/2002 | Peterson |
| 2003/0023299 A1 | 1/2003 | Amplatz et al. |
| 2003/0199919 A1 | 6/2003 | Palmer et al. |
| 2003/0167068 A1 | 9/2003 | Amplatz |
| 2003/0220666 A1 | 11/2003 | Mirigian et al. |
| 2004/0044361 A1 | 3/2004 | Frazier et al. |
| 2004/0049210 A1 | 3/2004 | Vantassel et al. |
| 2004/0193206 A1 | 9/2004 | Gerberding et al. |
| 2004/0210194 A1 * | 10/2004 | Bonnette ............... A61B 17/22 604/167.06 |
| 2005/0004517 A1 * | 1/2005 | Courtney ........... A61K 31/7068 604/96.01 |
| 2005/0065484 A1 | 3/2005 | Watson |
| 2005/0070952 A1 | 3/2005 | Devellian |
| 2005/0228434 A1 | 10/2005 | Amplatz et al. |
| 2005/0234543 A1 | 10/2005 | Glaser et al. |
| 2005/0288706 A1 | 12/2005 | Widomski et al. |
| 2006/0206139 A1 | 9/2006 | Tekulve |
| 2006/0206193 A1 | 9/2006 | Chobotov et al. |
| 2006/0241690 A1 | 10/2006 | Amplatz et al. |
| 2006/0247680 A1 | 11/2006 | Amplatz et al. |
| 2007/0055302 A1 | 3/2007 | Henry et al. |
| 2007/0066993 A1 | 3/2007 | Kreidler |
| 2007/0112380 A1 | 5/2007 | Figulla et al. |
| 2007/0135826 A1 | 6/2007 | Zaver et al. |
| 2007/0167980 A1 | 7/2007 | Figulla et al. |
| 2007/0179520 A1 | 8/2007 | West |
| 2007/0233186 A1 | 10/2007 | Meng |
| 2007/0239192 A1 | 10/2007 | Litzenberg et al. |
| 2007/0270891 A1 | 11/2007 | McGuckin, Jr. |
| 2008/0033480 A1 | 2/2008 | Hardert |
| 2008/0097495 A1 | 4/2008 | Feller, III et al. |
| 2008/0103585 A1 | 5/2008 | Monstadt et al. |
| 2008/0119887 A1 | 5/2008 | Que et al. |
| 2008/0249562 A1 | 10/2008 | Cahill |
| 2008/0262518 A1 | 10/2008 | Freudenthal |
| 2008/0281350 A1 | 11/2008 | Sepetka et al. |
| 2008/0306504 A1 | 12/2008 | Win et al. |
| 2009/0018562 A1 | 1/2009 | Amplatz et al. |
| 2009/0062845 A1 | 3/2009 | Tekulve |
| 2009/0082803 A1 | 3/2009 | Adams et al. |
| 2009/0187214 A1 | 7/2009 | Amplatz et al. |
| 2009/0209855 A1 | 8/2009 | Drilling et al. |
| 2009/0216263 A1 | 8/2009 | Tekulve |
| 2010/0010517 A1 | 1/2010 | Stopek et al. |
| 2010/0030200 A1 | 2/2010 | Strauss et al. |
| 2010/0106235 A1 | 4/2010 | Kariniemi et al. |
| 2010/0160847 A1 | 6/2010 | Braido et al. |
| 2010/0318097 A1 | 12/2010 | Ferrera et al. |
| 2010/0324586 A1 | 12/2010 | Miles et al. |
| 2011/0040324 A1 | 2/2011 | McCarthy et al. |
| 2011/0046719 A1 | 2/2011 | Frid |
| 2011/0082491 A1 | 4/2011 | Sepetka et al. |
| 2011/0118776 A1 | 5/2011 | Chen et al. |
| 2011/0265943 A1 | 11/2011 | Rosqueta et al. |
| 2011/0276080 A1 | 11/2011 | Nigon |
| 2011/0295298 A1 | 12/2011 | Moszner |
| 2011/0301630 A1 | 12/2011 | Hendriksen et al. |
| 2012/0041472 A1 | 2/2012 | Tan et al. |
| 2012/0046683 A1 | 2/2012 | Wilson et al. |
| 2012/0143008 A1 | 6/2012 | Wilkins et al. |
| 2012/0172928 A1 | 7/2012 | Eidenschink et al. |
| 2012/0215152 A1 | 8/2012 | Levine et al. |
| 2012/0245668 A1 | 9/2012 | Kariniemi et al. |
| 2012/0330341 A1 | 12/2012 | Becking et al. |
| 2012/0330348 A1 | 12/2012 | Strauss et al. |
| 2013/0012979 A1 | 1/2013 | Amplatz et al. |
| 2013/0018413 A1 | 1/2013 | Oral et al. |
| 2013/0085521 A1 | 4/2013 | Lim |
| 2013/0138136 A1 | 5/2013 | Beckham et al. |
| 2013/0190798 A1 | 7/2013 | Kapadia |
| 2013/0211443 A1 | 8/2013 | Cragg et al. |
| 2013/0245667 A1 | 9/2013 | Marchand et al. |
| 2013/0274868 A1 | 10/2013 | Cox et al. |
| 2014/0172001 A1 | 6/2014 | Becking et al. |
| 2014/0172004 A1 | 6/2014 | De Canniere |
| 2014/0222132 A1 | 8/2014 | Boucher et al. |
| 2015/0173770 A1 | 6/2015 | Warner et al. |
| 2016/0192912 A1 * | 7/2016 | Kassab ............ A61B 17/12181 606/200 |

FOREIGN PATENT DOCUMENTS

| | | | |
|---|---|---|---|
| EP | 1691879 B1 | 8/2006 | |
| EP | 1994887 A1 | 11/2008 | |
| JP | 2003529410 A | 10/2003 | |
| JP | 2007519498 A | 7/2007 | |
| JP | 2008536620 A | 9/2008 | |
| JP | 2012523943 A | 10/2012 | |
| WO | WO 2000/072909 A1 | 12/2000 | |
| WO | WO 2001/030266 A1 | 5/2001 | |
| WO | WO 2005/074814 A2 | 8/2005 | |
| WO | WO 2005/074814 A3 | 8/2005 | |
| WO | WO 2006/115689 A1 | 11/2006 | |
| WO | WO 2010/123821 A1 | 10/2010 | |
| WO | WO 2013/005195 A1 | 1/2013 | |
| WO | WO 2013/068466 A1 | 5/2013 | |
| WO | WO 2014/144980 A1 | 9/2014 | |
| WO | WO 2014/145005 A2 | 9/2014 | |
| WO | WO 2014/146001 A2 | 9/2014 | |
| WO | WO-2015100178 A1 * | 7/2015 | ............. A61B 17/22 |
| WO | WO-2017156083 A1 * | 9/2017 | ............. A61B 17/24 |
| WO | WO-2017161331 A1 * | 9/2017 | ........ A61B 17/00234 |

OTHER PUBLICATIONS

Japanese Patent Office, Office Action dated Jul. 6, 2022 with English translation in Japanese Patent Application No. 2019-565293, 12 pages.

WIPO, U.S. International Search Authority, International Search Report and Written Opinion dated Aug. 24, 2018 in International Patent Application No. PCT/US2018/034750, 9 pages.

* cited by examiner

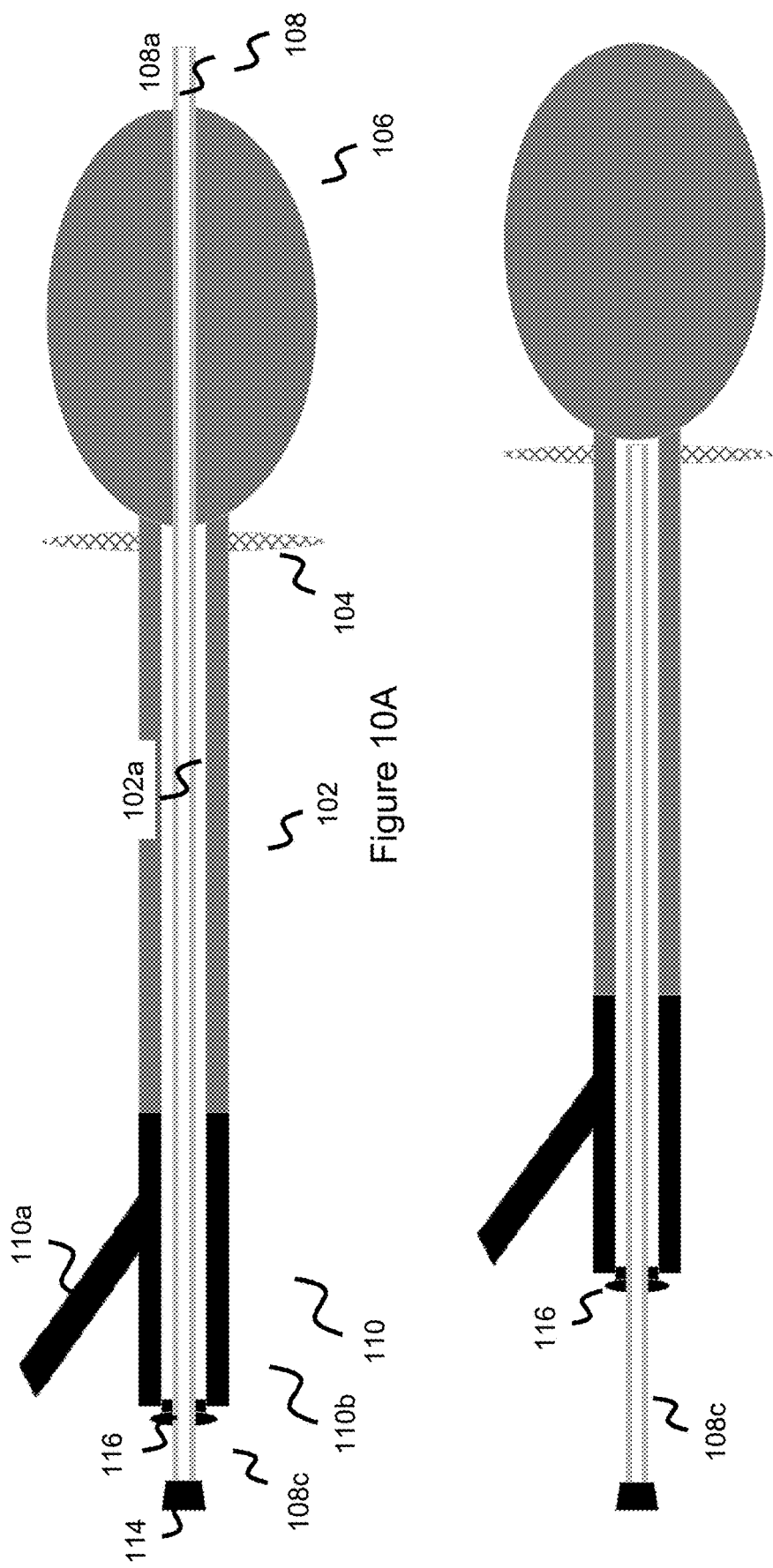

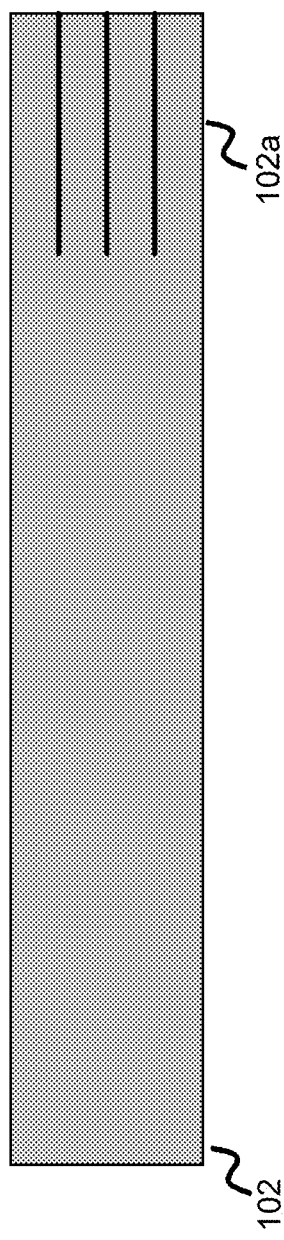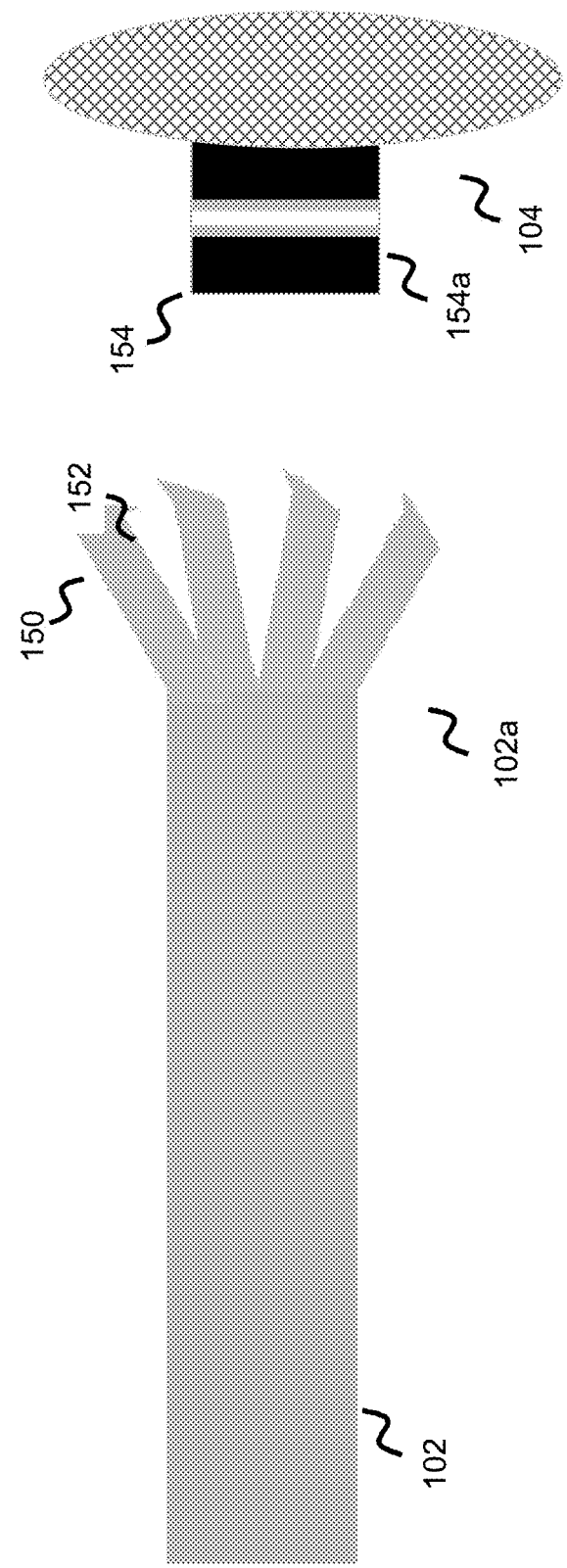

OCCLUSION SYSTEMS

RELATED APPLICATIONS

This application is a nonprovisional application of, and claims priority to, U.S. Provisional Application Ser. No. 62/754,493 filed Nov. 1, 2018 entitled Occlusion Systems, which is hereby incorporated herein by reference in its entirety.

BACKGROUND OF THE INVENTION

The Left Atrial Appendage (LAA) is a small ear-shaped sac in the muscle wall of the left atrium. For people with atrial fibrillation or an irregular heartbeat, the heart impulse is irregular which can cause blood to collect in the LAA and clot over time. These clots can later migrate out of the LAA potentially causing a stroke and other complications.

Occlusion is one method of treating an LAA, where a device or structure is placed within the LAA to limit blood flow into the LAA. These occlusive structures fill the LAA space and thereby prevent blood accumulation and clot formation in the area. However, LAA's can be difficult to treat since they typically form complex, irregular shapes thereby making occlusion or filling of the structure difficult. Furthermore, since the LAA abuts the heart, the region is highly volatile and subject to high pulsation pressure, thereby making it difficult to keep any occlusive device at the target site without migrating. These factors make it difficult to occlude the LAA.

Embolic coils are small coils which fill the target space and are used for occlusive purposes in other areas of the vasculature (e.g., neurovascular aneurysms). These coils are not, however, suitable for placement in a LAA due to the tendency for the coils to migrate due to the odd shape of the LAA, the typically wide ostium or neck region of the LAA, the high pulsation pressure and the proximity of the LAA to the heart.

To address the high pulsatile pressure of the region, some occlusive devices specifically designed to treat LAA's utilize barbs to anchor within the LAA to thereby resist migration. These barbs can puncture the vessel wall and cause bleeding, which can lead to additional complications. Other devices forego these anchors, but then suffer from poor apposition relative to the LAA due to the high pulsatile forces and odd shape of the region.

There is a need for a device which can effectively treat LAA's without the above-enumerated complications while also addressing other deficiencies of the prior art devices not specifically discussed herein.

SUMMARY OF THE INVENTION

The invention relates to occlusive devices that can be used to treat a variety of vascular complications, with the presented embodiments having particular utility with regard to the LAA.

In one embodiment, an occlusive device utilizes a balloon or expandable occlusive structure which can be used to treat problems associated with the LAA, among other vascular conditions. In one embodiment, the balloon is conformable to the geometry of the LAA. In another embodiment, the balloon is more rigid to provide a firmly occlusive structure to restrict the entry of matter into and out of the LAA. The balloon can comprise a variety of shapes, including circular, elliptical, and/or conical/teardrop shapes.

In one embodiment, the occlusive device utilizes a balloon or expandable occlusive structure, and further utilizes a proximal barrier structure to seal the neck or ostium of the treatment site (e.g., LAA ostium). In one embodiment, the occlusive device includes a first port connected to a proximal portion of the balloon and a second port connected to a distal portion of the balloon. In one embodiment, the first port is used to deliver an inflation fluid (e.g., saline or contrast agent) to fill the balloon, while the second port is used to deliver an adhesive which is used to help bind the balloon to the treatment site. In one embodiment, the first and second ports are releasably connected to the occlusive device via a selective detachment mechanism.

In one embodiment, the occlusive device utilizes a balloon with a permeable layer, such as a permeable layer either used on a portion of a balloon or bonded to a portion of the balloon. The permeable layer is porous and allows adhesive or other bonding material delivered through the balloon to permeate to the surface, thereby aiding in binding the balloon to the target treatment site (e.g., LAA tissue).

In one embodiment, the occlusive device utilizes two balloons—an inner balloon fillable with inflation fluid and an outer balloon fillable with adhesive. The outer balloon is porous to allow adhesive to bind the outer balloon to the tissue of the target treatment site.

In one embodiment, a magnetic occlusion device/system is utilized. An implant which occludes the LAA utilizes magnetic strips of a first polarity. A magnetic device utilizing a magnet of a second, opposite polarity is tracked to a region adjacent to the LAA, and the attraction between the magnets binds the implant to the wall of the LAA, thereby aiding in retaining the implant to the LAA.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which:

FIG. 10A illustrates an occlusive device including an adhesive delivery member in an extended state, according to one embodiment.

FIG. 10B illustrates an occlusive device including an adhesive delivery member in a retracted state, according to one embodiment.

FIG. 17A illustrates an outer tubular member used in an occlusive device in a collapsed configuration, according to one embodiment.

FIG. 17B illustrates an outer tubular member used in an occlusive device in an expanded configuration, according to one embodiment.

DESCRIPTION OF EMBODIMENTS

The embodiments presented herein have particular utility to treating conditions associated with a left atrial appendage (LAA). As described above in the background section, conditions associated with the left atrial appendage are difficult to treat since they are located near the heart and therefore are associated with high pulsatile pressure making it difficult to keep an occlusive device in the target area without migrating. Furthermore, the LAA often has an irregular shape making sizing and occluding the area difficult.

Figure 1:
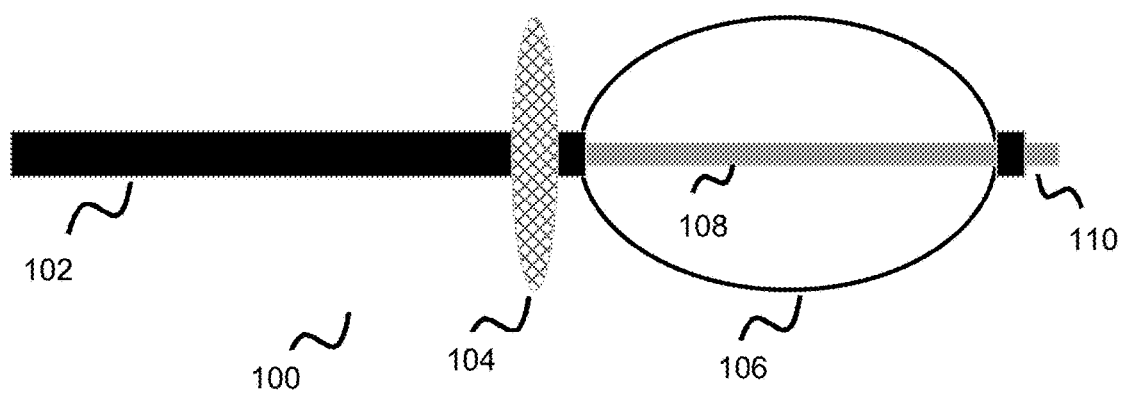
FIG. 1 illustrates an occlusive device comprising a balloon, according to one embodiment.

The following embodiments are generally geared toward an occlusion device utilizing an inflatable object such as a balloon to occlude the treatment site/LAA. FIG. 1 shows an occlusion device 100 which includes a balloon 106 on a distal portion of the device. Occlusion device 100 includes a proximal elongated member 102 connected to the proximal end of balloon 106. This elongated member 102 contains a channel or lumen used to convey inflation fluid (e.g., contrast agent, saline, or a gaseous substance) into the balloon. Element 102 functions both as a pusher to pushably deliver the occlusive device 100, while also containing the fluid delivery lumen used to convey inflation fluid to inflate the balloon 106. In this way, elongate element 102 serves multiple functions, and can be considered a pusher element as well as a fluid conduit.

A smaller inner elongated member 108 spans through and past the first elongated member 102 and sits at or beyond a distal end of the balloon. This inner member 108 is used to deliver an adhesive which will help bind the balloon to the tissue of the target region, as will be explained in more detail later. Occlusive device 100 also includes a proximal support member/barrier 104. Barrier 104 is sized to sit within a proximal portion of the treatment site (e.g., at or within the neck/ostium region of the LAA) and provides a further barrier to prevent blood from flowing into the treatment site.

Figure 2:
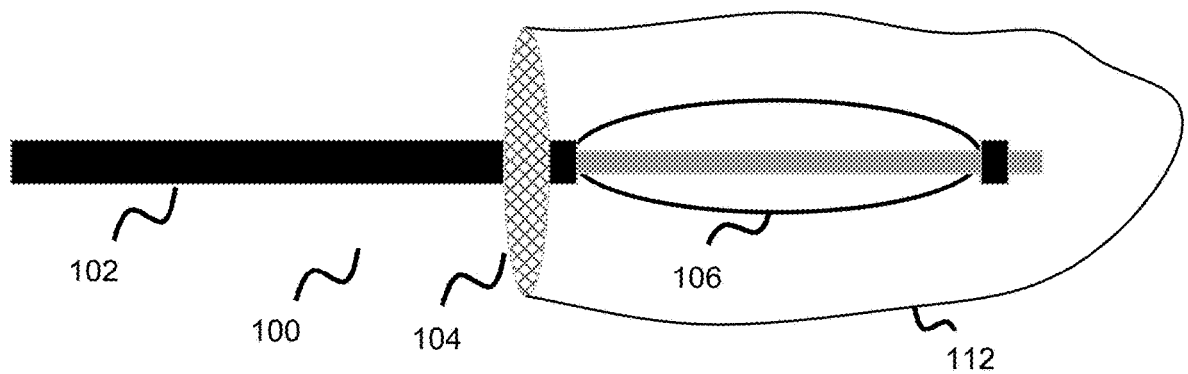
FIG. 2 illustrates the occlusive device of FIG. 1 with the balloon in an uninflated configuration, according to one embodiment.
Figure 3:
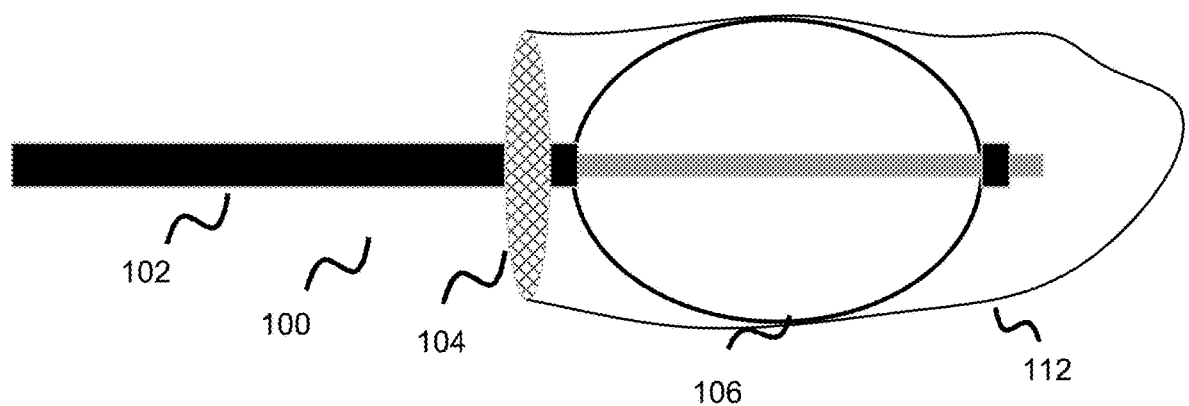
FIG. 3 illustrates the occlusive device of FIG. 1 with the balloon in an inflated configuration, according to one embodiment.
Figure 4:
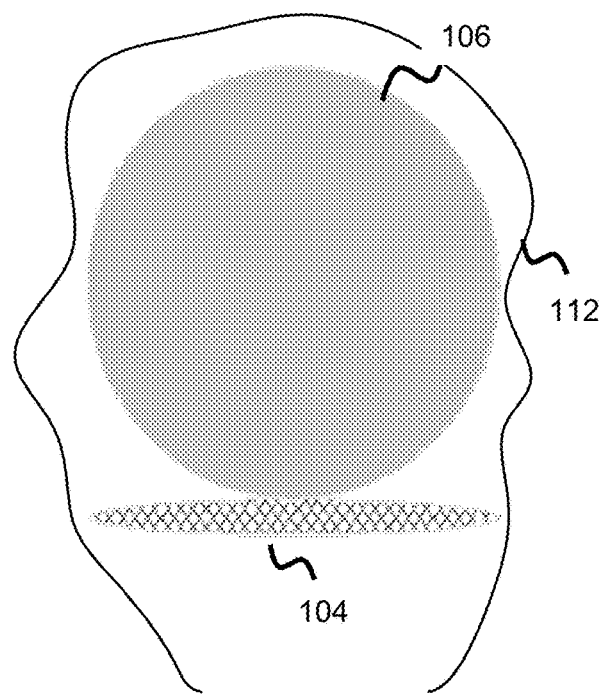
FIG. 4 illustrates an implanted occlusive device in a target treatment region, according to one embodiment.

The occlusion device 100 is delivered to an LAA treatment site, as shown in FIG. 2 where the balloon 106 is delivered within the LAA 112. The user would use the elongate element/pusher 102 to maneuver the device through a larger overlying delivery catheter and into the LAA cavity 112. The balloon is then inflated, as shown in FIG. 3 (e.g. by conveying inflation fluid via lumen 102 into balloon 106) to inflate/expand the balloon to occlude the LAA treatment site 112. The device 100 is positioned such that barrier 104 sits at the neck or ostium of the LAA, or within the LAA (preferably within the LAA cavity abutting the neck region, however, the geometry of the LAA cavity will likely affect the position of the barrier element 104). The position of the device when the barrier 104 is physically within the LAA is shown in FIG. 4. Since the purpose of the neck barrier is to provide sufficient occlusion at/near the neck/ostium of the LAA, the barrier 104 is preferably seated at the neck or within the LAA cavity near the neck region to help prevent blood entry into the LAA. Furthermore, the barrier provides a scaffold for tissue growth which, over time, helps permanently close off the LAA.

In one embodiment, the neck barrier element 104 is composed of a mesh of metallic (e.g., nitinol or stainless steel) wires which are wound into a flattened disc-type shape. To aid in radiopacity and imaging of the device, barrier 104 can alternatively be composed of radiopaque wires (e.g., platinum, palladium, tantalum, or gold) or utilize a mesh comprising both metallic non-radiopaque, and metallic radiopaque wires. In one embodiment, a polymer layer (e.g., PTE or PTFE) is utilized inside the mesh layer. This polymer layer is porous, where these pores are sized to restrict blood passage but promote tissue growth. In one example, these pores can be sized from about 10-40 microns, where pores in this range will limit blood passage while promoting tissue growth. The porous polymer layer can be created in various ways. For example, a polymer layer can be stretched to impart these pores. Alternatively, a spun microfiber processing technique or open-foam technique can be used to create a porous polymer. In one embodiment, an anti-thrombogenic coating is used over the mesh, this coating can be configured or engineered to prevent clot formation while also promote tissue/endothelial growth. Examples include PMEA/poly(2-methoxyethylacrylate) and X-coating.

Figure 5A:
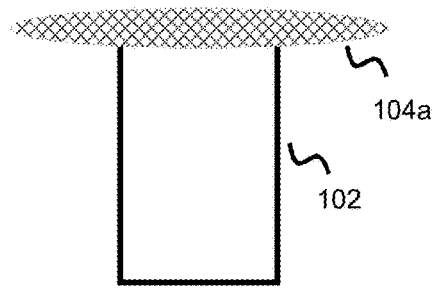
FIGS. 5A-5B illustrate a barrier element used in an occlusive device, according to one embodiment.
Figure 5B:
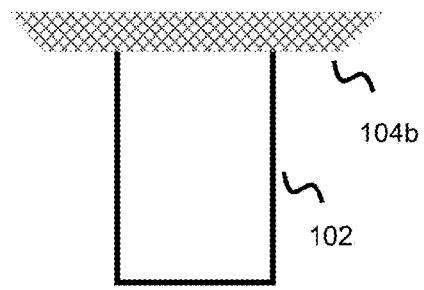

Alternative configurations for the barrier element 104 can utilize a projecting ridge around the circumference of the disc. In this way there is more of a saucer-like or cup-like profile which helps prevent other embolic material or adhesive from migrating past the barrier element 104. These different shape configurations are shown in FIGS. 5A-5B, where FIG. 5A utilizes a flat-disc shaped barrier element 104a while FIG. 5B utilizes a barrier element with a ridged interface 104b to form a more saucer or cup-like shape. The barrier element 104b of FIG. 5B can either utilize a vertical wall surrounding a flat disc mesh, or an outwardly angled wall surrounding the flat disc mesh.

Figure 6:
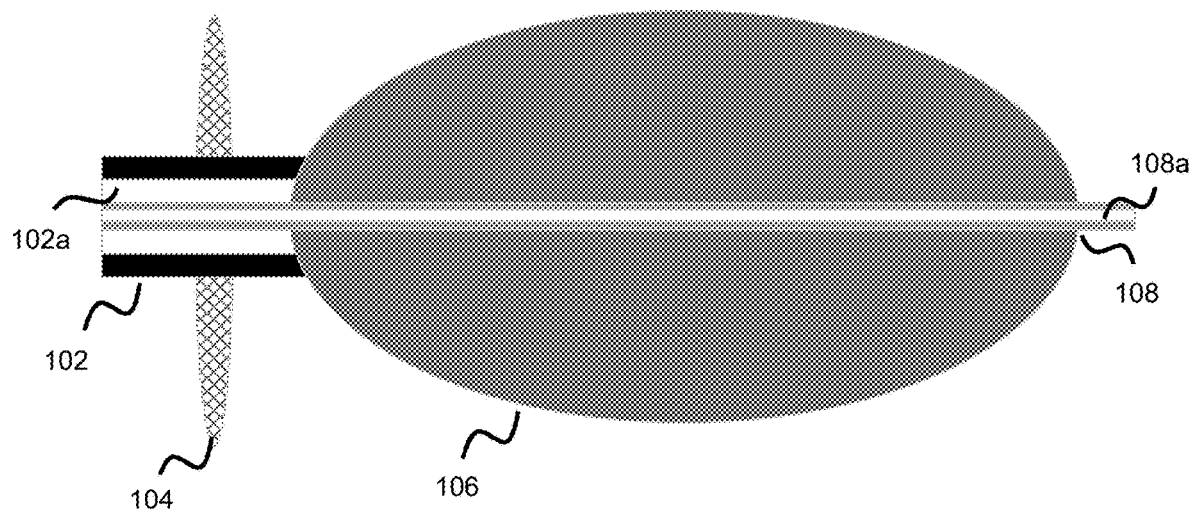
FIG. 6 illustrates an occlusive device including an inflation fluid delivery member and an adhesive delivery member, according to one embodiment.

The distal section of occlusive device 100 is shown in more detail in FIG. 6. Outer tubular member/pusher element 102 contains a lumen 102a. Within this lumen there is a smaller tubular member 108 which spans the length of the pusher element 102 and distally beyond. The outer tubular member/pusher lumen 102a acts as a conduit for balloon inflation media delivered from the proximal end of the device. This media travels through the lumen 102a and distally into the balloon to fill it. The actual inflation fluid delivery space is the area between the inner surface of the pusher element 102 and the outer surface of inner tubular member 108, since the inner tubular member 108 occupies a portion of the interior of the pusher. Therefore, this is the free space that is available for the inflation media to travel.

Smaller/inner tubular element 108 acts a conduit for adhesive which is delivered through lumen 108a. The adhesive is delivered from a proximal end of the device and is delivered out from the distal end of the inner element 108.

Figure 7:
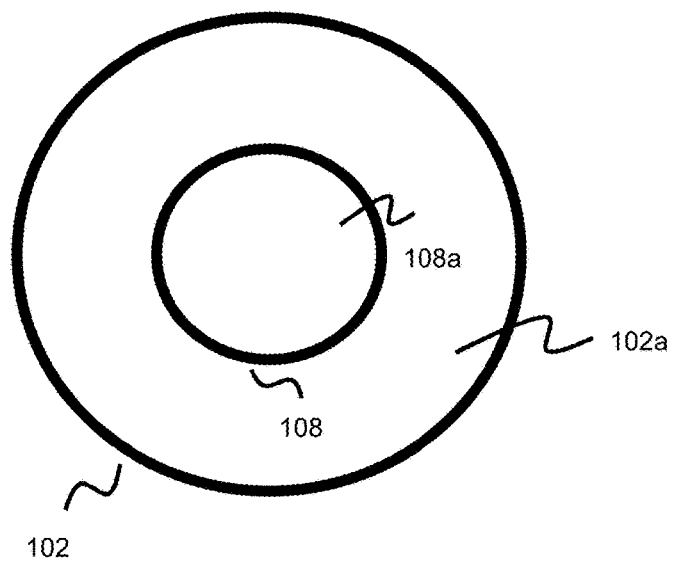
FIG. 7 illustrates a cross-sectional profile of the occlusive device of FIG. 6.

The adhesive, when delivered, will fill the target space between the LAA treatment site and the balloon, binding the balloon to the LAA tissue, thereby adhering the balloon to the LAA tissue and thereby promoting occlusion of the LAA. FIG. 7 shows a cross sectional view of the various lumen components as they sit within pusher/outer tubular element 102, with inflation lumen 102a comprising the area around inner tubular element 108 and adhesive lumen 108a.

Figure 8:
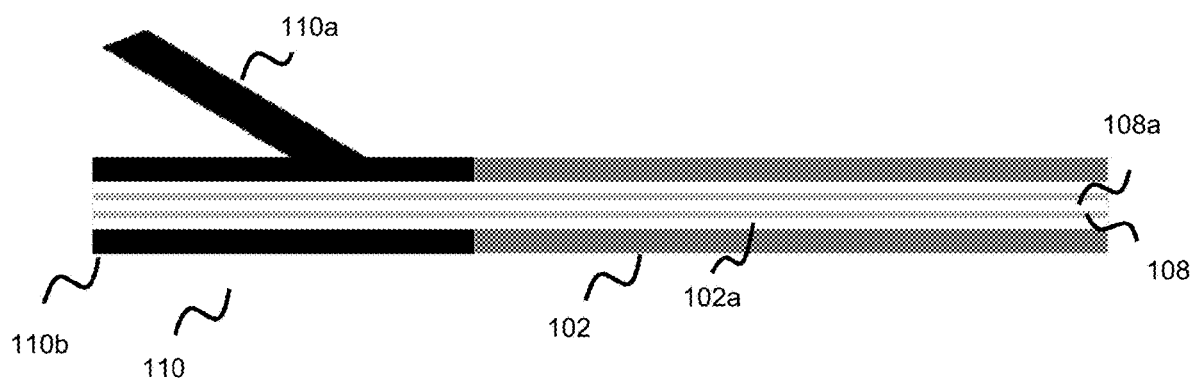
FIG. 8 shows a proximal end of the occlusive device of FIG. 6.

The proximal section of the occlusive device is shown in more detail in FIG. 8. The proximal end of the outer tubular member 102 is connected to a hemostatic valve or y-adapter 110. The y-adapter includes two ports 110a and 110b facilitating connection to two separate fluid-containing vessels (e.g., syringes). The first port 110a is enabled for connection to an inflation-media (e.g., contrast agent or saline) containing syringe. Port 110a contains an internal channel which is linked with lumen 102a to convey the inflation media into the balloon to inflate the balloon. The second port 110b is enabled for connection to an adhesive-containing syringe. Port 110b contains an internal channel which is linked with lumen 108a to convey the adhesive through the lumen and out distally from the balloon at the exit port location, as shown in FIG. 5, where the adhesive helps retain the balloon to the tissue wall of the treatment site.

In an alternative configuration, the association is flipped whereby port 110a is used to deliver adhesive through lumen 108a, and port 110b is used to deliver inflation media to the balloon through lumen 102a. In this alternative configuration, the lumen through port 110a is linked to inflation lumen 102a, while the lumen through port 110b is linked to adhesive port 108a.

When the occlusion procedure takes place, the occlusive balloon 106 and mesh barrier portion 104 are tracked to the treatment site (e.g., LAA) so that the still-uninflated balloon is placed within the volume of the LAA while the mesh barrier portion 104 also preferably is placed at a more proximal location within the volume of the LAA so as to provide an occlusive barrier (both to blood entering, and later to adhesive potentially seeping out) although it should be noted in some treatment scenarios it may be desirable to keep the mesh barrier portion 104 outside the neck/ostium of the LAA.

Radiography/angiograms/imaging can be used to confirm proper placement of the occlusive balloon within the LAA. The user will then fill the balloon, for instance, by using an inflation-media containing syringe connected to one port of the y-adapter to deliver inflation fluid through inflation lumen 102a into the balloon.

The user can confirm proper inflation of the balloon through various channels, including imaging and/or tactile monitoring (such as feeling resistance from further inflation as the balloon contacts the surrounding tissue).

When sufficient inflation of the balloon confirmed, the user then injects adhesive through the other port of the y-adapter (e.g. via a connected adhesive-containing syringe) such that it is conveyed through adhesive lumen 108a and distally projected beyond the distal end of the balloon 106. After delivery, the adhesive will flow around the exposed outer surface of the balloon and between any space between the balloon and the surrounding tissue, thereby binding the balloon to the tissue. The adhesive is delivered past the distal end of the balloon given that the terminal end of the adhesive delivery port is beyond the distal end of the balloon (as shown in FIGS. 3 and 5) or otherwise relatively flush with the distal end of the balloon, and, as such, the distal portion of the balloon is the part that will first contact the adhesive.

Figures 9A, 9B:
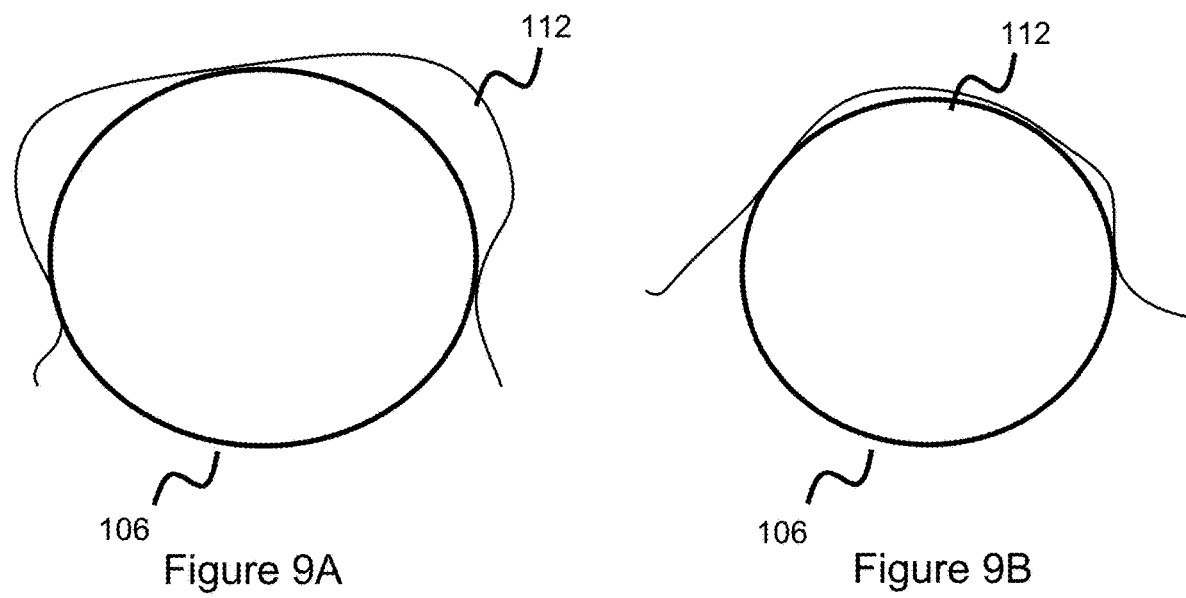
FIGS. 9A-9A show an occlusive balloon's placement in a treatment site, according to one embodiment.

The balloon's position relative to the geometry of the LAA is shown in FIGS. 9A-9B, which show exemplary distal LAA wall shapes and how the balloon would be positioned relative to the distal section of the LAA. Note how the more proximal portion of the balloon will be in direct apposition to the LAA while there may be open space around the distal section of the balloon, between the balloon and the LAA tissue. As such, any delivered adhesive will likely fill this "open" space and be blocked by the portion of the balloon which directly contacts the vessel. As such, there is minimal risk of adhesive flowing proximally past the entire balloon surface. However, the barrier element 104 can provide a further barrier to adhesive migration in, for example, situations where the adhesive happens to seep past the balloon/wall interface, or in scenarios where the LAA has a particularly complex or tortuous shape thereby making continuous apposition with the LAA wall difficult. Furthermore, the adhesive preferably is configured to harden relatively quickly upon contact with blood/the balloon, thereby minimizing the risk of adhesive migration.

A variety of compounds can be used for the adhesive, including acrylic-resin adhesives (e.g., n-butyl cyanoacrylate, octyl cyanoacrylate, isobutyl cyanoacrylate, methyl cyanoacrylate, ethyl cyanoacrylate), epoxy/epoxy resins (e.g., those sold under the trade names Epotek or Masterbond), fibrin glues (e.g., that sold under the trade name Dermabond), silicone adhesives (e.g., NuSil), or light curable adhesives (e.g., Dymax MD or Masterbond UV10). Where UV/light activated adhesive are used, the distal section of adhesive delivery lumen 108 can include appropriate lighting and appropriate circuitry, or the balloon itself can utilize lights to cure or harden the adhesive. US Pub. No. 2018/0338767 discloses various ways to include lighting on a delivery conduit to cure light (e.g., UV) sensitive adhesives, and is incorporated by reference in its entirety. This reference provides various examples of how one would configure a light system in coordination with an adhesive delivery system.

The balloon 106 is filled with gaseous or liquid inflation media (e.g., saline or contrast agent). One advantage of using liquid contrast agent as an inflation media is that in some situations it will help better visualize the balloon relative to the treatment site (e.g., LAA cavity) to make sure the balloon is properly filled and occluding the treatment site. In one embodiment, a liquid inflation media (e.g., saline or contrast agent) is delivered through a syringe configured for attachment directly to (by directly mating to) a particular port (e.g., port 110a of the y-adapter 110 of FIG. 8) or indirectly to a particular port (e.g., through a connecting element bridging port 110a and the syringe). In one example, the syringe and port utilize corresponding male/female mating structures (e.g., threads and recesses) to enable connection. In another embodiment, the balloon is filled with gaseous inflation media delivered through a canister, and the port (e.g. port 110a, or an attachment structure linked to port 110a to enable connection between the port and canister) contains a needle to pierce the port. The canister is filled with, for example, compressed air, oxygen, nitrogen, or carbon dioxide which travels through lumen 102a to fill the balloon.

The occlusion system can comprise a kit of parts, including syringes containing adhesives and inflation media. In one embodiment, a kit includes a first pre-filled syringe with adhesive and another pre-filled syringe with inflation media (e.g., contrast agent or saline), configured such that the user can simply attach the syringe to the respective ports of the y-adapter 110. In another embodiment, a kit includes a first container with adhesive and another container with inflation media, and separate syringes where the user would prepare the syringes by adding the adhesive to a first syringe and adding the inflation media to a second syringe, where these syringes are then connected to the respective y-adapter ports.

The previous description has focused on the occlusive device and how it is configured to allow the balloon to inflate and to allow adhesive to be delivered to attach the balloon to the surrounding tissue of the treatment site. Since the balloon 106 and mesh barrier 104 remain within the LAA space to occlude it, they must be detachable from the rest of the pusher/outer tubular member 102 system after the balloon is filled and any adhesive delivered. To enable this, the inner adhesive delivery member 108 is movable from a first extended configuration where it is flush with the distal tip of the balloon 106 or distally beyond balloon 106 (depending on the particular delivery configuration), to a second retracted configuration where it is in a more-proximally oriented position relative to outer member 102 to enable detachment.

Figure 10C:
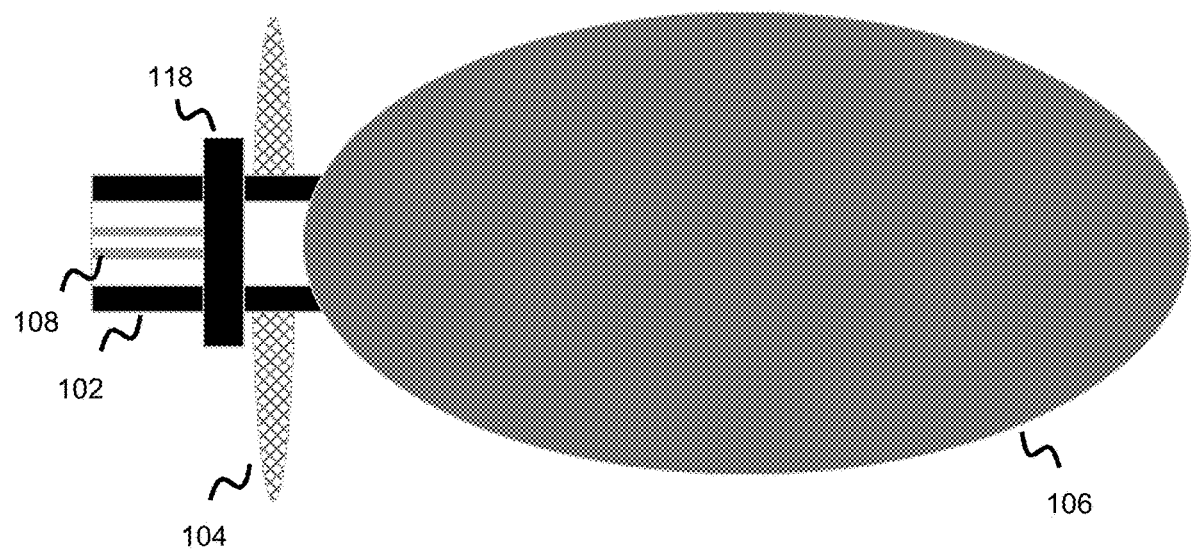
FIG. 10C illustrates an occlusive device including a detachment junction, according to one embodiment.

FIG. 10A shows the first, extended configuration of inner member 108. Inner member 108 projects proximally from port 110b and includes a proximal exposed portion 108c, and a syringe hub 114 configured for attachment to an adhesive-containing syringe which is used to deliver adhesive through lumen 108a of inner member 108. In this delivery configuration, the inner member 108 is in an extended configuration whereby the inner member 108 is either flush with the distal tip of balloon 106, or projects distally beyond balloon 106 as shown in FIG. 10A. A collet mechanism 116 is connected to the proximal end of the hemostatic valve 110 and enables the user to, for example, rotationally engage a tightening mechanism on the collet to clamp down on inner member 108 to affix the inner member 108 relative to the outer member 102 and thereby prevent displacement.

Using the collet, the user can ensure the inner member 108 remains in its extended delivery configuration. In this configuration, the user would attach the syringe to hub 114 and deliver adhesive through lumen 108a of inner member 108. This would take place after delivering inflation media through the inflation lumen 102a to inflate balloon 106 as described earlier.

After balloon 106 is inflated and the user delivers adhesive through lumen 108a, the user would then release collet 116 (e.g., by rotating the collet's tightening mechanism in a direction to release the pressure against inner member 108). The user would then retract or pull back on the inner member 108, whereby the inner member adopts the configuration shown in FIG. 10B where the exposed section 108c increases in length while the inner member 108 retracts to a position at the distal tip of outer member 102 or proximal of the distal tip. A detachment junction 108 is part of the outer member 102 and located proximal of the barrier structure 104. Thermal, electrolytic, or mechanical means which are well known in the art can be used to sever, degrade, or release this detachment junction to sever the outer member 102 from the barrier 104 and balloon 106.

One such thermal detachment system is described in U.S. Pat. No. 8,182,506 which is hereby incorporated by reference in its entirety. In some embodiments, the detachment junction can comprise a meltable adhesive (e.g., when used with a thermal detachment system which heats the adhesive), a corrodible electrolytic junction (which corrodes or galvanizes in response to an electrolytic reaction to sever the junction), or a mechanical screw interface which is rotated in a first direction to unscrew the junction.

In one example of a thermal or electrolytic system, the outer member/pusher 102 would include one or two current-carrying wires spanning the length of the structure 102 and connected to a proximal battery to power the system and provide a voltage source. Once this detachment occurs, the barrier 104 and balloon 106 are kept within the LAA treatment site while the user can simply retract the now-detached pusher/outer member 102 to withdraw the rest of the system (including inner member 108) from the vasculature.

In alternative embodiments, the collet can be replaced or supplemented with a threaded rotational engagement mechanism between the inner member 108 and outer member 102. In this embodiment, the inner member 108 and outer member 102 would utilize male/female connective components (e.g. male projecting threads on the outer surface of inner member 108 and female receiving interface on outer member 102) whereby the user would simply rotate the inner member 108 to unscrew the inner member 108 from the outer member 102, and then be able to proximally retract the inner member. The user could then optionally engage the collet member to keep the inner member 108 affixed in its retracted position relative to pusher/outer member 102 while the disengagement procedure is conducted to disengage the outer member 102 from the deployed barrier 104 and balloon 106.

In one embodiment, instead of just being an open lumen, the distal region of outer member 102 utilizes a valve and this valve is only opened when inner tubular member 108 is propelled through and past the distal end of the outer tubular member 102. In this way, the inner tubular member 108 exerts force upon the valve to open it as the inner tubular member 108 is pushed distally to adopt the configuration shown in FIG. 10A. When the inner tubular member 108 is retracted proximally past the distal end of the outer member 102 (e.g., once the adhesive has been delivered and detachment will be initiated), this valve is then closed. In this way, inflation fluid delivery is only possible when the inner member 108 is positioned in such a way that it opens the valve element of the outer tubular element 102.

A variety of valve technologies known in the mechanical art can be used, for instance pressure, gate, butterfly, etc. In one embodiment, the occlusive device is provided in a state where the inner member 108 is positioned as shown in FIG. 10A, such that is in an adhesive delivery position. As such, the distal valve on outer member 102 is already opened, and can only close once inner tubular member 108 is proximally pulled within outer member 102.

The balloon element 106 is preferably comprised of a polymer material such as PTE or PTFE/ePTFE, the grade of polymer can depend based on the desired characteristics. In some embodiments, the balloon is comprised of a relatively soft/conformable material (e.g., a soft polymer) in order to conform to the unique geometry of the LAA to thereby occlude the LAA. In some embodiments, the balloon is comprised of a relatively stiff material (e.g., a stiffer or more rigid polymer) to provide a stiffer barrier material. This might be useful for circumstances where mesh barrier 104 is more porous (e.g., doesn't utilize an inner polymer layer or outer coating) and where, therefore, the balloon itself should also better help resist the flow of blood, or in an inventive embodiment where the mesh barrier 104 is not used at all and where the balloon itself would have to have some structural strength to resist the flow of blood. The latter scenario might be used where the geometry of the treatment site is such that the neck/ostium/opening to the treatment site (e.g., LAA) is much smaller than the maximum width of the treatment site, thereby making placement of the barrier element 104 difficult; or in scenarios where the treatment site geometry is such that strong apposition between the balloon and the tissue wall will occur, rendering the barrier element 104 superfluous. In one embodiment where no barrier element 104 is used, the balloon could even utilize a chemically bonded layer along the bottom portion of the balloon which is designed to promote tissue growth to seal off the neck with tissue, over time.

Figure 11A:
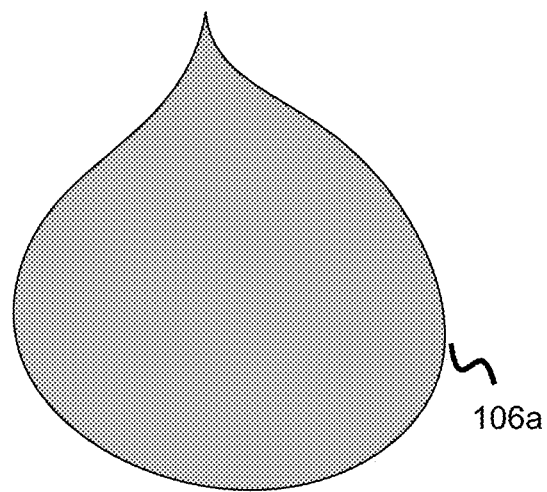
FIG. 11A illustrates a teardrop shaped balloon used in an occlusive device, according to one embodiment.
Figure 11B:
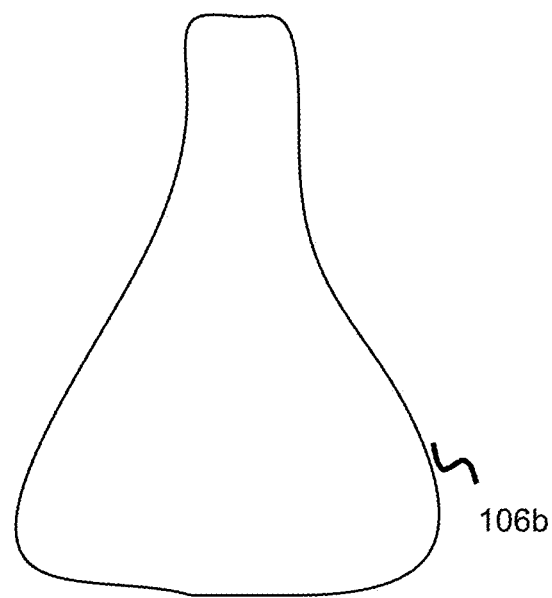
FIG. 11B illustrates a conical shaped balloon used in an occlusive device, according to one embodiment.

In one embodiment, the balloon when inflated has a circular or elliptical shape, as generally shown in the illustrative figure embodiments showing balloon 106. In another embodiment, the balloon when inflated has a teardrop-type shape 106*a* comprising a narrowed top/distal region, as shown in FIG. 11A. This type of shape is useful in circumstances where apposition between the tissue and balloon surface is desirable around the longitudinal middle section and/or proximal section of the balloon as opposed to the distal section of the balloon. In another embodiment, the inflated balloon has a conical-type configuration 106*b* as shown in FIG. 11B. Other balloon shape configurations are possible. A non-exhaustive list includes cylindrical, pyramidal, truncated-conical, other more complex geometrical shapes. The shape of the treatment site can influence the balloon shape, where particular shapes would provide enhanced occlusive effect for particular treatment site geometries.

To deliver the occlusive device 100, the device is first contained within a larger delivery catheter (not shown). The delivery catheter is tracked to the target treatment location (e.g., partially within the LAA cavity) and the delivery catheter is retracted or the pusher/outer member 102 of the occlusive device is pushed such that the barrier 104 and balloon 106 are released from the catheter and into the LAA cavity. The balloon is then filled with inflation media, any adhesive used to bind the balloon to the tissue wall is delivered, and the barrier 104 and balloon 106 are detached from the outer member 102 as discussed above.

Since the device is delivered through a catheter which is deployed partially within the LAA cavity, the barrier 104 can be oversized relative to the opening/neck of the LAA and still fit within the LAA. This oversizing of barrier 104 is possible because the device is sheathed into the LAA cavity and then unsheathed such that it will be already positioned within the LAA thereby allowing the barrier 104 which is already placed within the LAA cavity to collapse as needed to fit within the cavity. In one example, mesh barrier is sized to be about 1.5 times to 2.5 times the size of the opening of the LAA. This oversizing will allow the mesh barrier to potentially adopt a clustered configuration, meaning the barrier doesn't adopt its full shape, but instead adopts the configuration of FIG. 12 where the ends of barrier 104 extend upward due to the oversizing relative to the LAA 112 walls. Furthermore, this oversizing augments apposition with the tissue wall and helps ensure the barrier helps keep blood out of the LAA while also helping to keep material (e.g., adhesive) from migrating out from the LAA.

Figure 12:
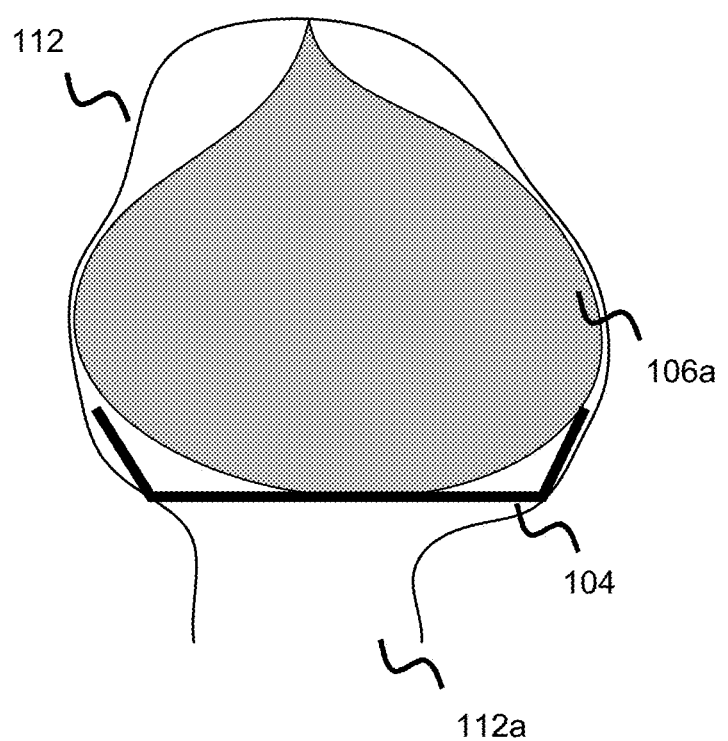
FIG. 12 illustrates the balloon of FIG. 11A in a treatment site, according to one embodiment.

In the particular configuration of FIG. 12, the neck or ostium 112*a* of the LAA 112 is smaller than the general sizing of the LAA further augmenting the blocking and occlusive effect of barrier element 104. However, even if the neck was larger or a similar size relative to the overall LAA, the barrier would still act as a sufficient occlusive barrier due to this general oversizing principle. Note, although FIG. 12 illustratively shows the tear-drop balloon shape of FIG. 11A, other balloon shapes can be used including the circular or elliptical shapes of the other figures, or the conical-type shape of FIG. 11B, among other shape profile possibilities.

Delivered adhesive will generally be affixed between the tissue wall and the outside surface of the balloon 106. However, it may be beneficial to provide a stronger adhesive hold by allowing the adhesive to permeate through part of the balloon. The following embodiments allow this by providing a distal permeable surface through which adhesive can flow to further augment adhesion between the balloon and adjoining/surrounding tissue.

Figure 13:
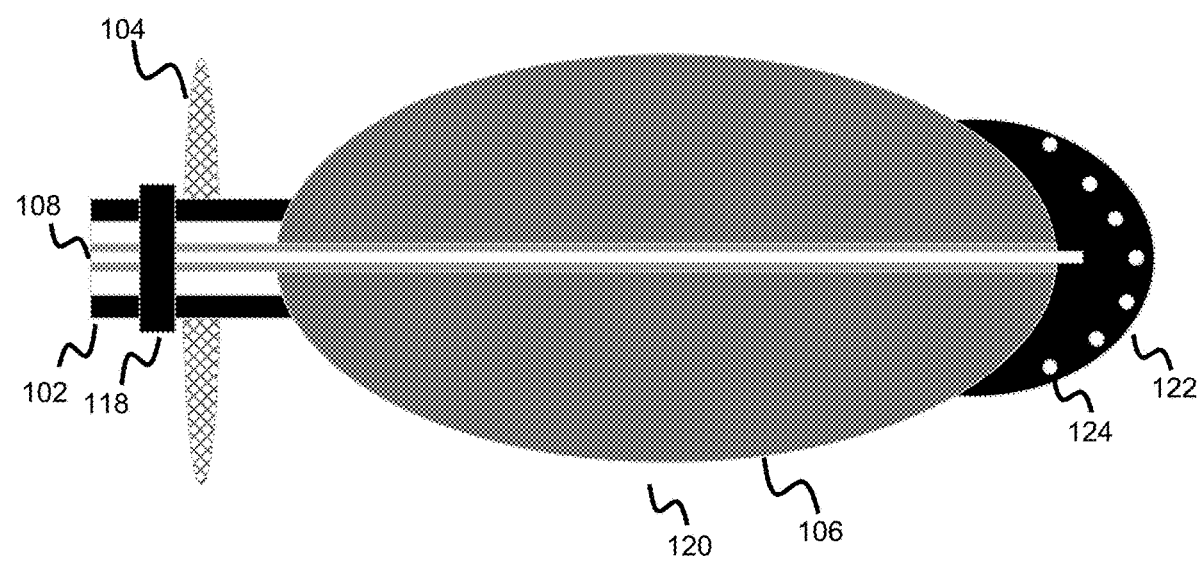
FIG. 13 illustrates an occlusive device including a balloon and a membrane, according to one embodiment.

FIG. 13 shows a distal portion of an occlusive device 120, generally similar to the embodiments of the occlusive device shown and described earlier utilizing a barrier 104, outer tubular member 102 which conveys inflation fluid to a balloon 106, and an inner tubular member 108 used to deliver adhesive. The occlusive device 120 further includes a distal membrane 122 distal of the balloon 106. The membrane 122 includes a plurality of pores or holes 124 which provide an exit path for adhesive which is delivered through the membrane. In this way membrane 120 can be considered permeable or semi-permeable.

The distal end of inner port/tubular member 108 is either flush with the distal end of balloon 106 or goes distally past this region but is within the volume defined by the membrane 122 such that the adhesive is delivered through and out of the membrane. In one example, the proximal portion of the membrane is bonded to the balloon and there is a gap between the balloon 106 and the distal portion of the membrane 122. The delivered adhesive goes through and out of the pores whereby the adhesive seeps out of the pores 124 of membrane 122 to bond at least the membrane 122 to the tissue of the treatment site.

The shape of the balloon 106 and size of the membrane 122 and pores 124 influence how much of the delivered adhesive gets beyond the membrane 122 to also bind the balloon. In some embodiments, the pores 124 are relatively localized in a small portion of the membrane 122 such that the bonding is primarily between the membrane 122 and the immediately surrounding tissue. In other embodiments, the pores 124 are spread throughout the membrane 122 whereby the adhesive is likely to flow past just the membrane portion and thereby also bond the more proximally positioned balloon 106 to the surrounding tissue.

As more of the adhesive is delivered through the membrane 122, there will be an adhesive barrier built up around the membrane whereby some of the adhesive will remain within the interior wall of the membrane and some will still be outside of the membrane. In this way a more effective hold is provided since the adhesive will partly permeate the interior of the membrane.

Various techniques can be used to create the porous membrane interface. For instance, a polymer (e.g., PTE, PTFE, or ePTFE) can be mechanically stretched to create small pores or holes, an electrospinning technique (e.g., PET spun microfiber) can be used to create the pores, or an open foam process can be used. The pores, in one example, are sized from about 10-180 microns. This embodiment utilizing membrane 122 would still utilize the movable inner lumen 108 which is proximally removed as discussed above to enable detachment of the barrier 104 and balloon 106 at detachment junction 118 after the balloon is inflated and any adhesive delivered. Similar to the earlier embodiments, balloon 106 can take on the teardrop or conical type shapes shown in FIGS. 11A-11B, or other shapes.

Figure 14:
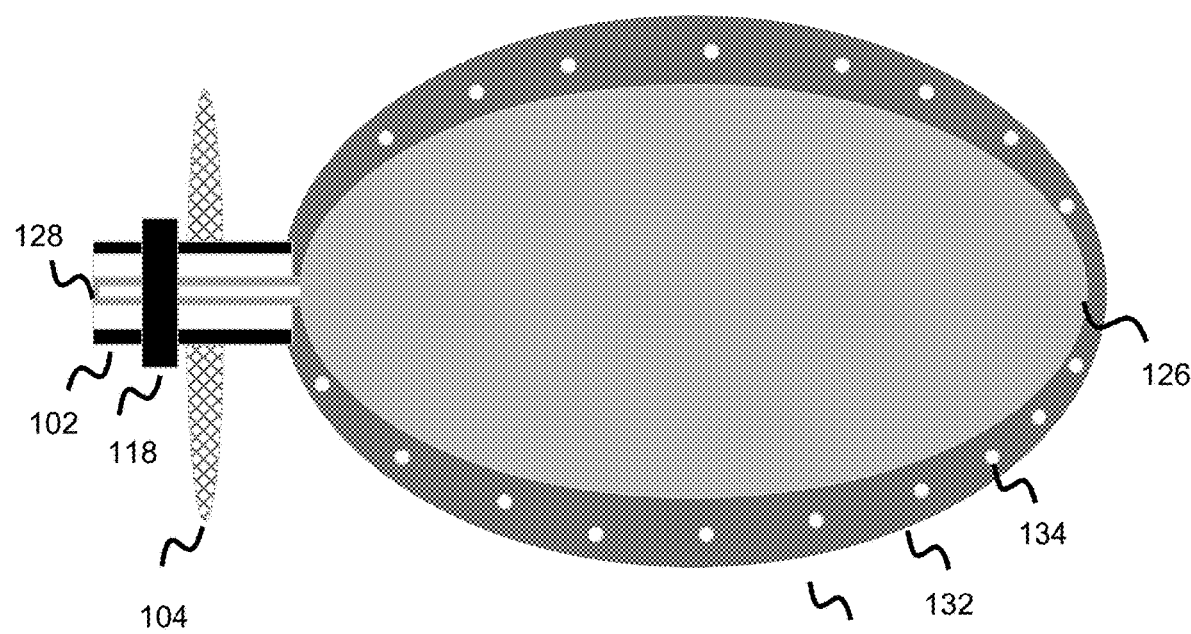
FIG. 14 illustrates an occlusive device including an inner and outer balloon, according to one embodiment.

Another embodiment, shown in FIG. 14, utilizes an occlusive device 130 having two overlapping balloons where an inner balloon 126 is filled with inflation fluid to inflate the balloon, while an outer porous balloon 132 is filled with adhesive. Inner balloon 126 is filled with inflation fluid (e.g., saline or contrast agent) delivered through inner tubular member 128 (note: in some previous embodiments, the inner member was used to deliver adhesive, however the configuration is flipped in this particular example). The filling of the inner balloon 126 in turn causes the overlying outer balloon 132 to also inflate. Once this filling step is done, adhesive is delivered through outer lumen 102 (note, as explained just above, this configuration is flipped from previously presented embodiments where the outer lumen functioned as an inflation lumen). Lumen 102 is connected to a proximal end of outer balloon 132 whereby adhesive flows in the space or volume defined by the area between the inner 126 and outer 132 balloons. Outer balloon 132 has a number of pores or holes 134.

In some embodiments, these pores 134 are substantially equally distributed over the entire area of the outer balloon 132—in other embodiments, these pores are substantially contained in/localized to one or more areas of the outer balloon 132 (e.g., a distal section of the outer balloon, or along the widest section of the outer balloon) corresponding to where tissue adhesion is most desirable. In some embodiments, the pores are concentrated along the distal and/or widest medial section of the balloon in order to limit the risk of adhesive flowing proximally beyond the balloon (though the barrier 104 would provide a further barrier to such migration, even if the pores 134 were more proximally placed). The pores allow adhesive to be contained on an interior and exterior region of the balloon in certain circumstances, thereby augmenting the adhesive effect.

The inflation/adhesive port configuration as discussed above regarding the FIG. 14 double-balloon embodiment can be flipped where an outer tubular member 102 is connected to inner balloon 126 while inner tubular member 128 is connected to outer balloon 132. In either circumstance, it will be desirable to be able to move inner member 128 after adhesive or inflation fluid delivery (depending on which is being delivered through the inner tubular member 128). These particular detachment concepts were discussed in the embodiments focused on the proximal end of the system discussed earlier and shown in FIGS. 10A and 10B and can also be used here. Similar to the previously presented embodiments, a detachment junction 118 proximal of the neck barrier element 104 is used. Furthermore, either or both the inner 126 and outer 132 balloons can adopt the more conical or tear-drop type profile shown in FIGS. 11A-11B, or other geometric shapes.

The previous embodiments have generally related to a balloon occluder used to occlude a target treatment space, such as an LAA, where several embodiments have utilized an adhesive to adhere the balloon to the tissue. The following embodiments utilize concepts where non-adhesive means can be used to retain the balloon against the surrounding tissue.

Figure 15:
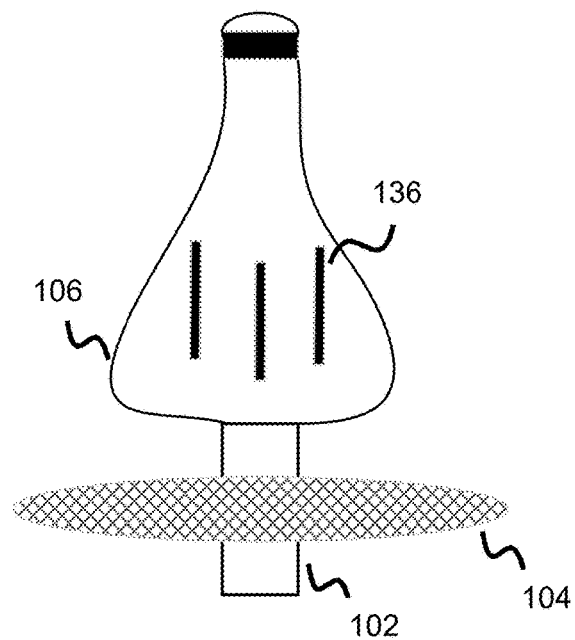
FIG. 15 illustrates an occlusive device including a balloon with magnetic elements, according to one embodiment.

FIG. 15 shows an occlusive device comprising a balloon 106 similar to the previous embodiments, which can be filled with an inflation fluid. The balloon is showed with a conical or tear-drop type profile but can have a more elliptical/ovular/circular profile (similar to how the more rounded balloon shapes pictured in other embodiments can also have a more conical or tear-drop type profile). The balloon includes one or more magnets 136 attached to the exterior surface of the balloon.

Figure 16:
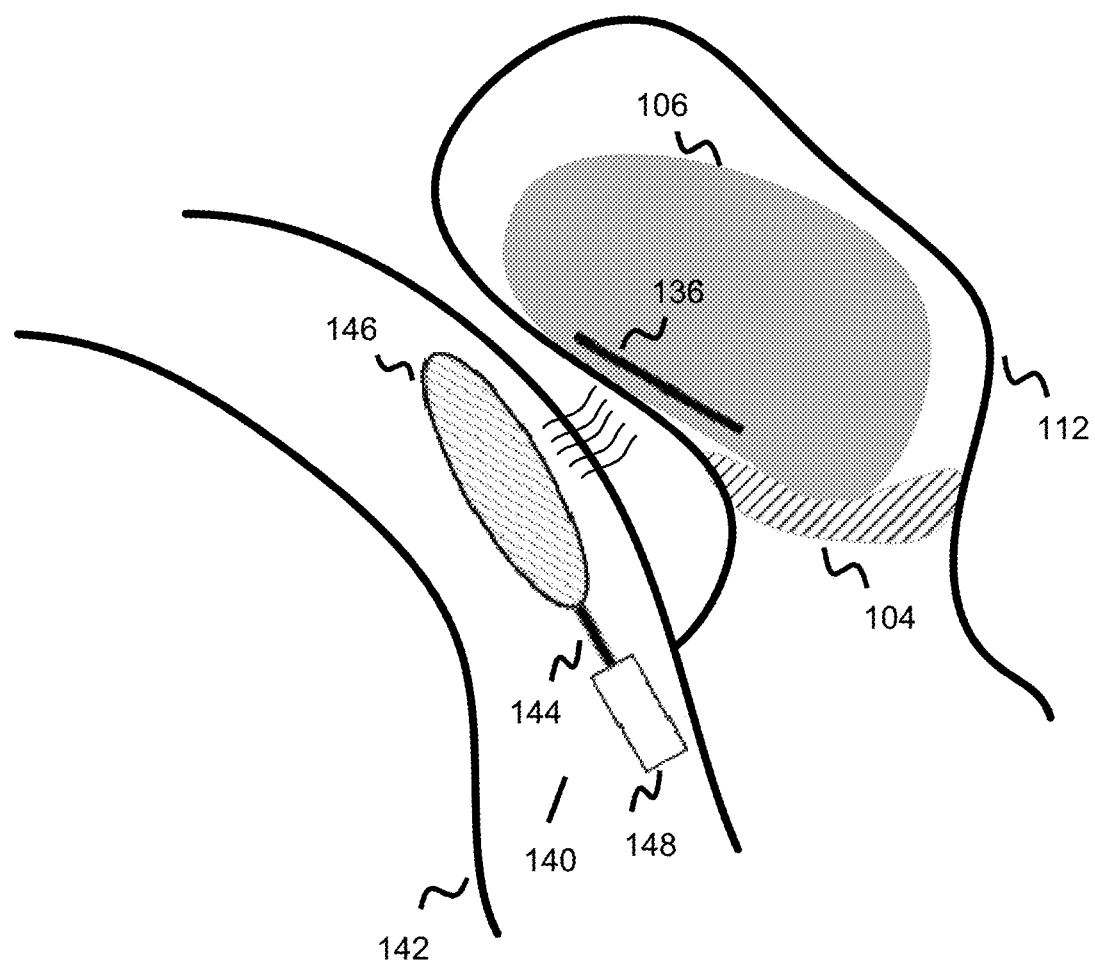
FIG. 16 illustrates the occlusive device of FIG. 15 used in a treatment region, according to one embodiment.

The operating principal is that a magnet of a first polarity is used on the balloon while a magnet of a second polarity is tracked through the adjacent vessel to urge the balloon against the LAA wall to help seat the balloon to the surrounding tissue. This is represented in FIG. 16, where a barrier element 104 and a balloon 106 including at least one magnetic element 136 are placed within an LAA 112. A magnetic deployment system 140 is deployed in a vessel adjacent the LAA (e.g. the upper pulmonary vein) such that the system 140 is across from the balloon 106.

The magnetic deployment system 140 includes a magnet 146 of a second polarity opposed to the first polarity of the balloon magnet 136, a pusher 144, and a catheter 148 used to track the magnetic system 140. The two magnets 136, 146 attract thereby encouraging the balloon to move against the LAA wall 112 and toward the magnet 146 in the second adjacent blood vessel 142. The magnet 146 can then be detached from the pusher 144 and the pusher 144 and catheter 148 then withdrawn so that the magnet 146 stays as a small, permanent implant. Alternatively, the magnetic system can be used as a supplemental system in addition to the ones specified above where the magnetic system is used as an additional step to help ensure the balloon 106 adheres to the vessel wall, and where the magnet 146 is removed once proper apposition between the balloon and LAA wall is determined.

Earlier parts of the description discussed ways to sever the outer tubular member 102 (see FIG. 10C, for example) from the barrier element 104 and balloon 106 once the balloon occlusion part of the procedure is completed via a detachment junction 118, such that the barrier element and balloon remain implanted in the LAA. The following embodiments relate to concepts that relate to alternative detachment systems.

FIG. 17A shows an outer tubular member 102 used as part of a detachable occlusive device. Outer tubular member 102 functions similarly as the outer tubular member of the previous embodiments in that it acts as a conduit for a fluid (e.g., inflation media) while releasably connected to a barrier element and balloon which comprise the implantable portion of the occlusive device. The outer tubular member includes a distal section 102a which adopts a first collapsed configuration as shown in FIG. 17A and a second expanded configuration as shown in FIG. 17B.

The distal portion 102a of the outer tubular member 102, in one example, has longitudinal cuts made along the circular periphery it to create a number of split sections 150. An enlarged mass is placed within the circumferential space and heat set to create an expanded shape as shown in FIG. 17B. Note, the split sections 150 are shown as flat since the image is two dimensional, however since tubular member 102 is a tube, these sections would actually be circumferential around the circumference of tubular member 102.

Each section 150 includes a projection or tooth 152. The projection 152 can either be at the distal tip of the distal section 150 or a bit proximal of the distal or terminal end (in other words, recessed a bit). The barrier element 104 and balloon (not shown) include a proximal projecting connection segment 154 which normally links with the rest of the outer tubular member 102. The connection segment 154 includes a grooved or recessed portion 154a.

When the distal portion 102a of outer tubular member 102 is in its collapsed delivery configuration of FIG. 17A, the tooth 152 of each segment 150 is engaged within the grooved portion 154a to keep the distal segment 150 of the outer tubular member 102 engaged with the connection segment 154. A button, knob, slider, or other actuation mechanism is used at the proximal end of the system where this actuation mechanism is engaged to cause the distal segments 150 to expand to thereby release the outer tubular member 102 from the barrier 104 (and balloon which is not shown) to thereby deploy and release the implant within the treatment site.

In one example, a plurality of pull wires span an external portion, internal portion, or a structural liner/wall of tubular member 102 to convey force between the user actual mechanism (e.g., knob, slider, or button) and the expandable/collapsible distal attachment sections 150. Where pull wires are used, engaging the actuation mechanism will result in a proximal or pulling force against the distal sections 150 which result in the released, open-jaw type configuration shown in FIG. 17B.

In some embodiments, a user would practice methods utilizing the occlusive device embodiments discussed and described above to occlude a treatment site. These steps would involve tracking the occlusive device through a larger delivery catheter and then exposing the device from a distal end of the delivery catheter.

For an LAA, this would involve placing the distal end of the delivery catheter in the LAA and then retracting the catheter, pushing the outer tubular member 102 to propel the occlusive device forward and out of the delivery catheter, or some combination of the two in order to expose the occlusive device.

The user would then inflate the balloon, for instance by engaging a syringe in connection with a first port of the hemostatic valve to deliver inflation fluid through the inflation lumen and into the balloon. Where adhesive is used as part of the procedure, the user would then deliver adhesive, for instance by engaging an adhesive-containing syringe or container in connection with a second port of the hemostatic valve to deliver adhesive through the adhesive lumen such that the balloon engages with the adhesive to retain to the tissue of the LAA.

The user would then initiate a detachment procedure, for instance by engaging detachment junction 118 or by utilizing the detachment concept described and shown in FIGS. 17A and 17B in order to deploy the occlusive device. The proximal portion of the device, now separated from the occlusive device, is withdrawn out of the vasculature.

Though the embodiments presented herein are described primarily with regard to occluding LAA's, these embodiments also have utility to treat a variety of vascular issues via occlusion. A non-exhaustive list includes aneurysms, fistula, arterio-venous malformation, atrial septal defect, patent foramen *ovale*, vessel shutdown procedures, fallopian tube issues, etc.

The device embodiments can be sized depending on the procedure being conducted. In one embodiment used for LAA occlusion purposes, the balloon occlusion device is sized to fit within a 12 French sheath, by way of example.

What is claimed is:

1. An occlusion device to occlude a treatment site comprising:
    a balloon;
    an inflation fluid delivery member that delivers inflation fluid to inflate the balloon;
    an adhesive delivery member that delivers adhesive to bind the balloon to the treatment site, wherein the adhesive delivery member is disposed radially within the inflation fluid delivery member; and,
    a porous membrane distal to the balloon, wherein the porous membrane is permeable or semi-permeable to the adhesive.

2. The occlusion device of claim 1, wherein the porous membrane is connected to a distal end of the balloon and defines a volume.

3. The occlusion device of claim 2, wherein a distal end of the adhesive delivery member is positioned within or open to the volume defined by the porous membrane.

4. The occlusion device of claim 1, wherein a proximal portion of the porous membrane is bonded to the balloon and forms a gap between the balloon and the porous membrane.

5. The occlusion device of claim 1, wherein the adhesive delivery member is removable from the balloon.

6. The occlusion device of claim 1, wherein the porous membrane is a PET spun microfiber.

7. The occlusion device of claim 1, further comprising a detachment junction between the balloon and the inflation fluid delivery member to detach the balloon from the inflation fluid delivery member.

8. The occlusion device of claim 1, further comprising a valve within the inflation fluid delivery member and through which the adhesive delivery member may be positioned through and removed from.

9. The occlusion device of claim 1, further comprising a mesh barrier disposed proximal to the balloon.

10. The occlusion device of claim 9, wherein the inflation fluid delivery member is detachable from the mesh barrier and the balloon.

11. The occlusion device of claim 1, further comprising an outer balloon in communication with the adhesive delivery member.

12. The occlusion device of claim 11, wherein the outer balloon is porous, wherein the outer balloon is configured such that the adhesive is permeable through the porous outer balloon.

13. An occlusion device to occlude a treatment site comprising:
    a balloon;
    an inflation fluid channel that delivers inflation fluid to the balloon;
    a porous membrane connected to the balloon and defining an interior volume; and,
    an adhesive delivery channel having a distal end opening within the interior volume and that delivers adhesive to bind the balloon to the treatment site, wherein the adhesive delivery channel is concentric within the inflation fluid channel.

14. The occlusion device of claim 13, wherein the interior volume defined by the porous membrane is located only at a distal portion of the balloon.

15. The occlusion device of claim 13, wherin porous membrane is disposed around the balloon to form a second outer balloon.

16. The occlusion device of claim 13, further comprising a detachment junction between the ballon and the inflation fluid channel to detach the balloon from the inflation fluid channel.

17. An occlusive device to occlude a treatment site comprising:
    a balloon;
    an inflation fluid channel that delivers inflation fluid to the balloon;
    a detachment junction between the balloon and the inflation fluid channel to detach the balloon from the inflation fluid channel; and,
    an adhesive delivery channel having an opening distal to the entire balloon and that delivers adhesive to bind the balloon to the treatment site.

18. The occlusive device of claim 17, wherein the adhesive delivery channel is removable from the balloon.

19. The occlusive device of claim 18, further comprising a porous membrane connected to the balloon and defining a distal volume; and wherein the adhesive delivery channel has the opening within the distal volume.

* * * * *